United States Patent
Kosh

(10) Patent No.: US 7,628,157 B2
(45) Date of Patent: Dec. 8, 2009

(54) ANTERIOR TRUNK SUPPORT OR HARNESS

(75) Inventor: Matthew Kosh, Seattle, WA (US)

(73) Assignee: Bodypoint, Inc., Seattle, WA (US)

( * ) Notice: Subject to any disclaimer, the term of this patent is extended or adjusted under 35 U.S.C. 154(b) by 102 days.

(21) Appl. No.: 11/140,814

(22) Filed: May 31, 2005

(65) Prior Publication Data

US 2005/0274388 A1    Dec. 15, 2005

Related U.S. Application Data

(60) Provisional application No. 60/579,471, filed on Jun. 14, 2004.

(51) Int. Cl.
  A61B 19/00 (2006.01)
  A61F 5/37 (2006.01)
  A41D 1/04 (2006.01)
  A41F 9/00 (2006.01)

(52) U.S. Cl. .................. 128/874; 128/869; 128/873; 128/875; 2/102; 2/311; 2/312; 2/327

(58) Field of Classification Search ............. 128/869, 128/874, 873, 875; 2/102, 311, 312, 327
See application file for complete search history.

(56) References Cited

U.S. PATENT DOCUMENTS

| | | | | |
|---|---|---|---|---|
| 1,617,604 A | * | 2/1927 | Hazelton et. al. | 156/164 |
| 2,727,278 A | * | 12/1955 | Thompson | 264/46.4 |
| 2,940,443 A | * | 6/1960 | Baker | 128/874 |
| 3,213,893 A | * | 10/1965 | Bellmore | 139/419 |
| 3,276,431 A | * | 10/1966 | Murcott | 128/874 |

(Continued)

FOREIGN PATENT DOCUMENTS

BE    1002357 A    1/1991

(Continued)

OTHER PUBLICATIONS

Adaptive Equipment Systems, "AES ComforFit® Anterior Posture Supports," accessed at http://www.aesys.com/quote/pdf/mkt3003. pdf 2 pgs (Apr. 2004).

(Continued)

*Primary Examiner*—Patricia M Bianco
*Assistant Examiner*—Tarla R Patel
(74) *Attorney, Agent, or Firm*—Townsend and Townsend and Crew LLP

(57) ABSTRACT

An anterior trunk support. The anterior trunk support is shaped like a vest and is formed of non-stretch or limited stretch material over a lower portion that extends over the upper belly and lower ribs of a user, and stretch material that extends from the non-stretch material to over the shoulders of the user. In this manner, a wearer may lean slightly forward, with the stretchable shoulder portion flexibly permitting such movement. The lower section may be stretchable in a width dimension only. As such, the lower section provides movement for user's respiration, thus providing additional comfort. By not stretching in the vertical direction, the anterior trunk support does not slide up the wearer's chest when tension is applied to the upper stretchable material. Thus, comfort is maintained, and the lower section does not approach the neck of the user.

20 Claims, 3 Drawing Sheets

U.S. PATENT DOCUMENTS

| | | | |
|---|---|---|---|
| 4,330,152 A | | 5/1982 | Legan et al. |
| 4,832,053 A | * | 5/1989 | McCarthy .................. 128/869 |
| 5,397,171 A | | 3/1995 | Leach |
| 5,495,621 A | * | 3/1996 | Kibbee ........................... 2/2.5 |
| 5,540,239 A | | 7/1996 | McClellan |
| 6,000,395 A | * | 12/1999 | Brown ................... 128/202.19 |
| 6,081,924 A | * | 7/2000 | Ott ................................. 2/102 |
| 6,086,551 A | * | 7/2000 | Allen .......................... 602/19 |
| 6,582,412 B2 | * | 6/2003 | Christoffel et al. ..... 604/385.01 |
| 6,691,351 B1 | | 2/2004 | Wharton |

FOREIGN PATENT DOCUMENTS

| | | |
|---|---|---|
| DE | 3708300 C | 10/1988 |

OTHER PUBLICATIONS

International Search Report by the EPO in corresponding PCT application (Dec. 22, 2005).

* cited by examiner

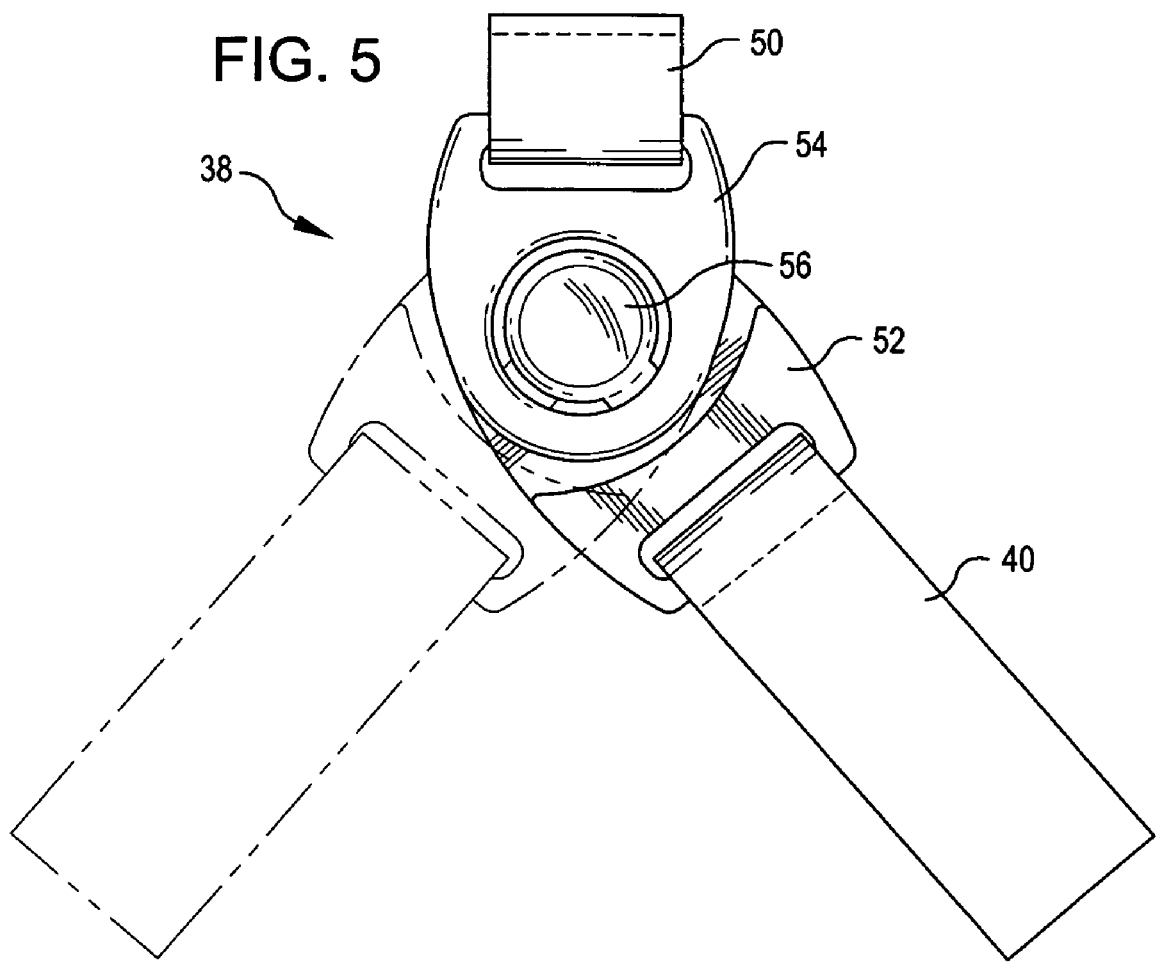

ANTERIOR TRUNK SUPPORT OR HARNESS

REFERENCE TO RELATED APPLICATION

This application claims the benefit of U.S. Provisional Application No. 60/579,471, filed Jun. 14, 2004, entitled "Anterior Trunk Support or Harness," and incorporated herein by reference.

TECHNICAL FIELD OF THE INVENTION

The present invention relates to body harnesses and supports, and more particularly an anterior trunk support or harness.

BACKGROUND OF THE INVENTION

In general, an anterior trunk support is a device that provides upper trunk control or support. Most prior art anterior trunk supports utilize a belt, strap, panel, or harness. Each of these is formed of a flexible material and is designed to comfortably fit around a user and to hold that user in an upright position, for example connected to a wheelchair.

Although prior anterior trunk supports work well for their intended purpose, often they rigidly hold the user in position, allowing little to no movement from the upright position. Although this function is desired in some applications, some users may have upper body movement, and may prefer limited support instead of restrictive control.

Conversely, some anterior trunk supports are formed entirely of a soft, elastic material such as neoprene. Such designs allow a great deal of movement but sacrifice the support needed by users with diminished muscle tone or spastic movement. Furthermore, because the lower portion of these entirely elastic anterior supports is able to stretch, the device rides up when the user leans forward, rubbing against the user's neck and creating a choking hazard.

SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In accordance with an embodiment, an anterior trunk support is provided. The anterior trunk support is shaped like a vest and is formed of multiple materials, for example stretch and non-stretch or limited stretch materials. Each material has a "unit stretch" (also known as "unit strain") which is a term well known in the art that is used to quantify the stretchability of a material. The unit stretch can be defined according to an equation wherein unit stretch (unit strain)=stretch (strain)/original length.

In accordance with an embodiment, non-stretch or limited stretch material extends over the upper belly and lower ribs of a user, and stretch material extends from the non-stretch material to over the shoulders of the user. In this manner, a wearer may lean slightly forward, with the stretchable shoulder portion flexibly permitting such movement. The stretchable material stretches with the user's shoulders, preventing the lower, non-stretch or limited stretch material from riding up the user's chest, and providing maximum comfort. Thus, unlike some prior art anterior trunk supports, a user is not rigidly locked in place. And unlike other prior art anterior trunk supports, the user is stabilized, but is still provided movement.

In accordance with an embodiment, the lower section of the anterior trunk support may have a low or zero unit stretch in the vertical direction with a larger unit stretch in the width direction so as to be, for practical purposes, stretchable in a width dimension only. As such, the lower section provides movement for user's respiration, thus providing additional comfort. By not stretching in the vertical direction, the anterior trunk support does not slide up the wearer's chest when tension is applied to the upper stretchable material. Thus, support is maintained, and the lower section does not approach the neck of the user.

The anterior trunk support may be used as a support (i.e., to position or hold an individual). Alternatively, the anterior trunk support may be used as a load-bearing harness, for attaching an item such as a backpack to a user.

Other features of the invention will become apparent from the following detailed description when taken in conjunction with the drawings, in which:

BRIEF DESCRIPTION OF THE DRAWINGS

FIG. 5 is a top view of the swivel buckle of FIG. 4, with the swivel buckle shown attached.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
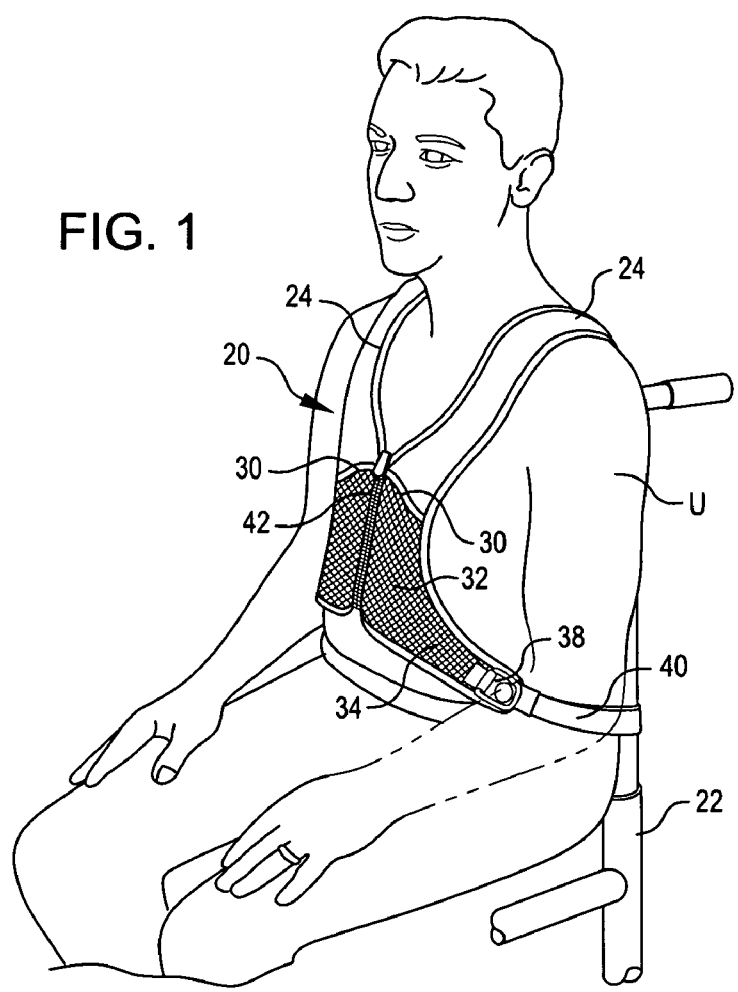
FIG. 1 is a side perspective view of an anterior trunk support vest in accordance with an embodiment of the invention, with the anterior trunk support vest shown on a user.

Referring now to the drawings, in which like reference numerals represent like parts throughout the several views, FIG. 1 shows an anterior trunk support vest 20 in accordance with an embodiment of the invention. In the drawings, the anterior trunk support vest 20 is worn by a user U sitting a wheelchair 22. However, the anterior trunk support vest 20 may be used for a number of other uses, for example for supporting a user against another device, or as a harness for attachment to a backpack or other item.

Figure 3:
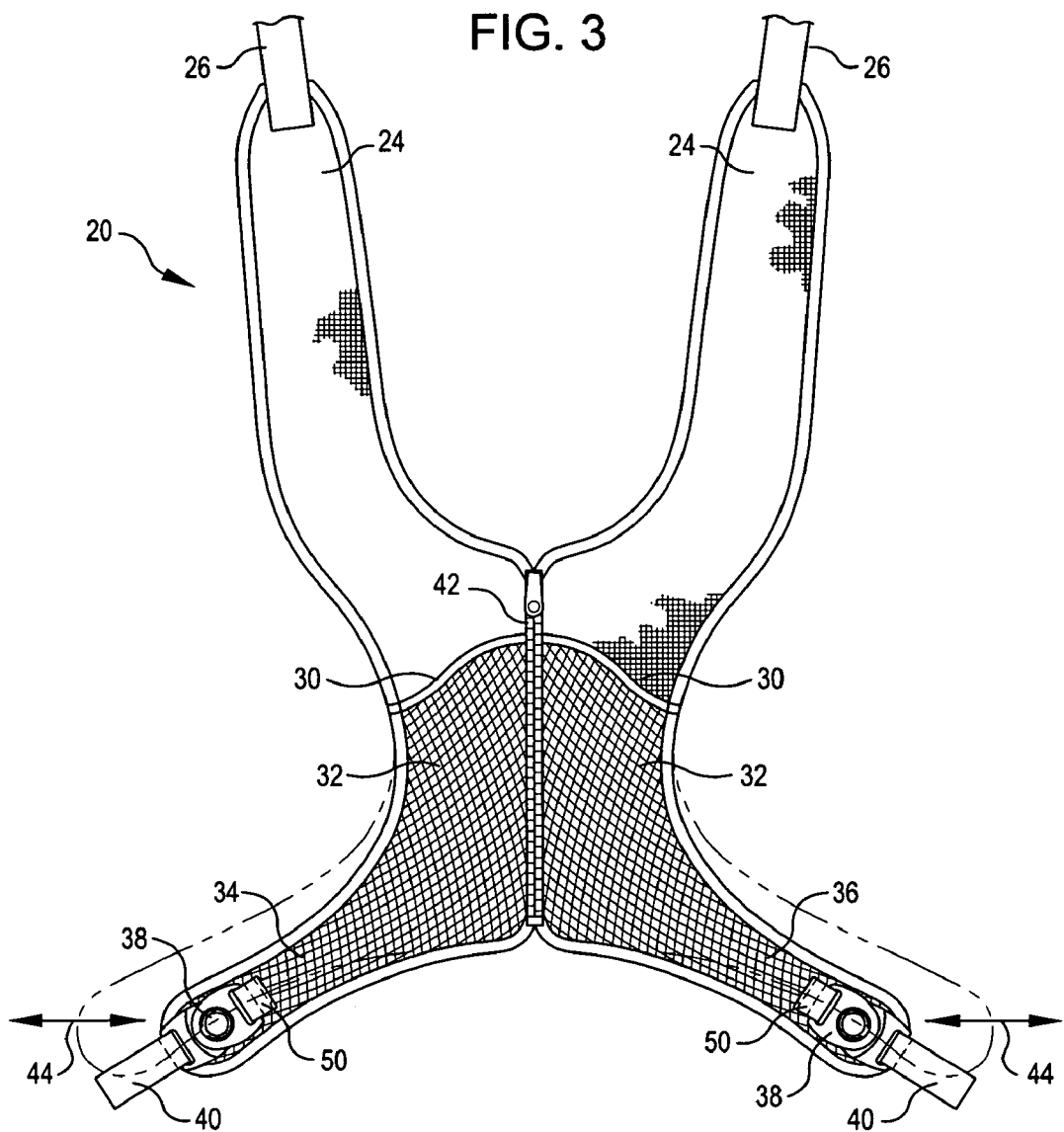
FIG. 3 is a front view of the anterior trunk support of FIG. 1, with the anterior trunk support extended flat.

As can be seen in FIG. 3, the anterior trunk support vest 20 includes shoulder straps 24 that are attached to top straps 26. The shoulder straps 24 extend downward to a convergence zone 30 where the shoulder straps 24 are attached to a lower portion 32 of the anterior trunk support vest 20. The convergence zone 30 is the area at which or line along which the lower portion 32 attaches to the shoulder straps 24.

The lower portion 32 is adapted and configured to fit around a trunk of a user U, and more specifically an upper portion of the belly of the user U up to and covering a lower portion of the ribcage of the user. The lower portion 32 includes two extensions 34, 36 that extend outward to sides of the user U. Swivel buckles 38 are attached by loops 50 at the ends of these extensions 34, 36. Lower straps 40 are attached to opposite sides of the swivel buckles 38 from the loops 50.

The top straps 26 are attached to a structure, for example to a top of the back of the wheelchair 22. The lower straps 40 are also attached to a structure, for example to a bottom of the back of the wheelchair 22, or to another suitable structure.

In the embodiment shown, the shoulder straps 24 are located on opposite sides of a zipper 42. The zipper 42 also divides the lower portion 32. The zipper 42 provides an easy way for a user, such as the user U, to install and remove the anterior trunk support vest 20.

In accordance with an embodiment, the shoulder straps 24 are formed of a stretchable material, such as elastomeric foams, also known as foamed rubber. Examples are chloroprene and Ethylene Propylene Diene Monomer (EPDM). Other stretchable materials may be used, including, but not limited to, spandex fabric and/or stretchable mesh fabric.

In accordance with an embodiment, the lower portion 32 is formed of a different material than the shoulder straps 24, and may, as an example, be formed of a non-stretchable material, such as a mesh material. In accordance with an alternate embodiment, the lower portion 32 is formed of a material that stretches in one direction indicated by the arrow 44 in FIG. 3: generally in the width dimension of a user.

The shoulder straps 24 and the lower portion 32 may be padded or insulated as desired to provide comfort and/or warmth for a wearer. However, such padding or insulation preferably would not hinder the stretchability of the shoulder straps 24 (and the lower portion 32, if stretching is provided).

In use, the anterior trunk support vest 20 is installed on a user, such as the user U, and provides support for the user U. The shoulder straps 24 fit on opposite sides of the users neck, and the lower portion 32 is positioned on the user's chest. The shoulder straps 24 and the lower portion 32 are adjusted, for example by cinching the top straps 26 and the lower straps 40. Alternatively, one of the lower straps 40 and top straps 26 may be fixed and the other cinched to adjust the anterior trunk support vest 20 against the user U. An end fitting buckle (not shown) may be used for cinching of each of the lower straps 40 and/or the top straps 26. An example of such an end fitting buckle is shown in U.S. Pat. No. 6,665,913, owned by the assignee of the present invention.

Figure 2:
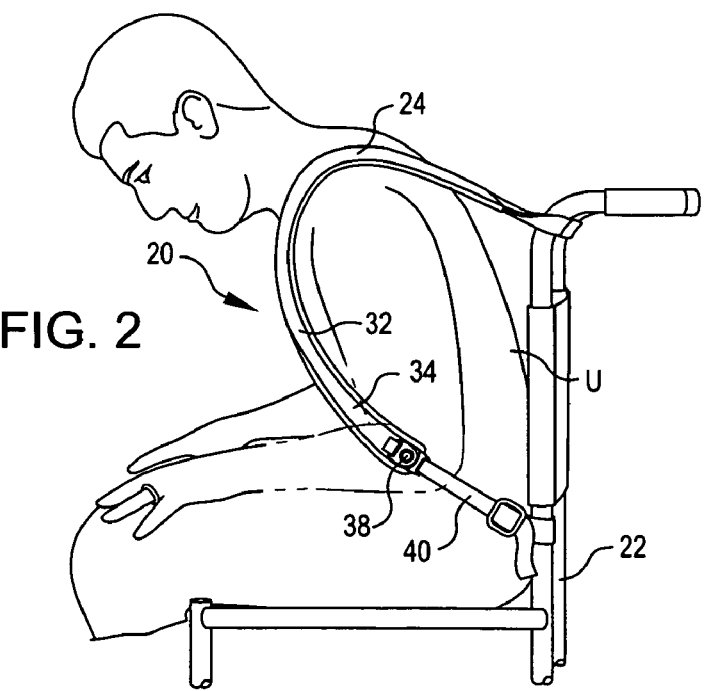
FIG. 2 is a side view of the anterior trunk support and user of FIG. 1, with the user leaning slightly forward.

The anterior trunk support vest 20 fits against the user U to support the user in an upright position. In accordance with an embodiment, however, the user U is free to lean forward against the resistance of the installed anterior trunk support vest 20, and in particular against the resistance of the stretchability of the shoulder straps 24. Because the shoulder straps 24 are stretchable, the user U can lean forward such as is shown in FIG. 2, without the lower portion 32 crawling upward on the torso of the user U. This feature permits some forward movement by the user U without the lower portion 32 crawling upward to the user U's neck. The amount that a user may lean forward is based upon the stretchability of the shoulder straps 24. A person of skill in the art may chose a suitable material for the shoulder straps 24 based upon the range of motion or level of function of the user U and a particular application.

Figure 4:
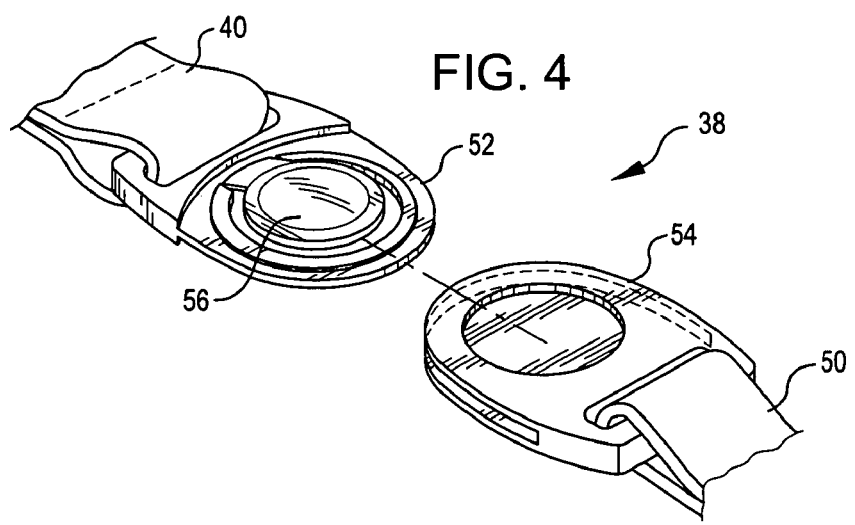
FIG. 4 is a side perspective view of a swivel buckle that may be used with the anterior trunk support of FIG. 1, with the swivel buckle shown detached.

As can be seen in FIG. 4, the swivel buckles 38 each include a male connector 52 and a female receiver 54. As is known, the male connector 52 may be inserted and snapped into the female receiver 54. The male connector 52 is then free to rotate relative to the female receiver 54, as shown in FIG. 5.

The male connector 52 may be removed from the female receiver 54 by depressing a tab at the center of the male connector 52.

The swivel buckles 38 provide convenience in that when the user U moves, such as leaning forward as is shown in FIG. 2, the lower straps 40 pivot to the most direct line of tension and avoid bunching of the anterior trunk support vest 20, which would cause discomfort. The swivel movement of the swivel buckles 38 is shown exaggerated in phantom in FIG. 5. This action can also be achieved by sewing the strap loosely to a D-ring or other suitable connection structure, but the use of the buckles 38 allows the lower straps 40 to be separated for removal.

If unidirectional stretchable material is used for the lower portion 32, the unidirectional material can provide ease in breathing for the user U, because it allows the chest of the user U to expand during respiration. An example of a unidirectional stretchable material is leno weave material, also known as gauze or doup weave. This material stretches primarily in one direction, but allows very limited stretching in another. Other suitable materials may be used. The material may be arranged so that the stretchable direction is aligned to extend the width of a user, such as the user U, and the limited stretch direction of the material is aligned vertically.

The convergence zone 30 is shaped to take maximum advantage of the stretchable qualities of the shoulder straps 24. As can be seen in FIG. 3, the convergence zone 30 is rounded into an S-shape so that at its outer portions it is perpendicular to the direction of extension of the shoulder straps 24, but at its central portion it approaches horizontal, or perpendicular to the zipper 42. The overall rounded shape of the convergence zone 30 is perpendicular to the extension of the shoulder straps 34. This configuration permits tension applied through the shoulder straps 24 to stretch and pull uniformly on the lower portion 32.

Although the anterior trunk support vest 20 has use for supporting a person, such as a seated person upright in the wheelchair 22, the anterior trunk support vest 20 may be used in other applications, such as for a load-bearing harness in backpacks, military equipment carrying vests, toolbelt supports, and in other applications where there is a need for a supportive harness which allows comfortable movement with minimal loss of control. The anterior trunk support vest 20 may include pockets or other structures for convenience of the particular application. For example, an anterior trunk support vest 20 used on a backpack for bicyclists may include pockets for a drinking tube and an anterior trunk support vest 20 designed for a fly fisherman's backpack may include pockets for various hooks and other fishing paraphernalia. In addition, the anterior trunk support vest 20 may be attached in a different manner, such as by being sewn directly onto a backpack or being attached directly to a toolbelt in the style of suspenders.

Other variations are within the spirit of the present invention. Thus, while the invention is susceptible to various modifications and alternative constructions, a certain illustrated embodiment thereof is shown in the drawings and has been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anterior trunk vest, comprising:
    a lower portion comprising a top section and a bottom section, the lower portion comprising a first material, and the lower portion being arranged and configured to extend over at least a portion of an upper belly and lower ribs of a user when the anterior trunk vest is worn by a user, the bottom section of the lower portion being adapted and configured, when a user is wearing the anterior trunk vest, to be secured around the user's left and right sides to a structure that is positioned at least partly behind the user;
    shoulder straps connected to the top section of the lower portion such that, when the anterior trunk vest is worn by the user, each shoulder strap is attached to the top section at a location on an anterior of the user, each shoulder strap comprising a second material and having a free end that is securable to the structure and each shoulder strap being configured to extend, when a user is wearing the anterior trunk vest and the shoulder straps are secured to the structure, from the top section over the shoulders of a user and to the structure, the second material being more stretchable in a vertical direction than the first material is stretchable in a vertical direction such that, when the anterior trunk vest is positioned on a user and the bottom section of the lower portion and shoulder straps are attached to the structure that is positioned at least partly behind the user, the user can lean forward away from the structure without the lower portion substantially crawling upward on the trunk of the user.

2. The anterior trunk vest of claim 1, wherein the first material comprises a leno weave fabric.

3. The anterior trunk vest of claim 1, wherein the first material is substantially more stretchable in a width direction than in a vertical direction.

4. The anterior trunk vest of claim 1, wherein the second material comprises foamed rubber.

5. The anterior trunk vest of claim 1, wherein the bottom section of the lower portion comprises swivel buckles for connecting the anterior trunk vest to the structure.

6. The anterior trunk vest of claim 1, wherein the anterior trunk vest is configured to be used as a harness.

7. The anterior trunk vest of claim 1, wherein the anterior trunk vest is configured to be used as a support.

8. The anterior trunk vest of claim 1, wherein the anterior trunk vest comprises a convergence zone for each side of the anterior trunk vest, the convergence zone located between the first material and the second material, the convergence zone for each side of the anterior trunk vest extending downward as the convergence zone extends outward when the anterior trunk support is worn by a user whose upper torso is upright.

9. A wheelchair comprising the anterior trunk vest of claim 1, wherein the structure is the wheelchair.

10. A backpack comprising the anterior trunk vest of claim 1, wherein the structure comprises the backpack.

11. An anterior trunk vest and structure combination, comprising:
    a structure;
    an anterior trunk vest comprising:
    a lower portion comprising a top section and a bottom section, the lower portion comprising a first material, and the lower portion being arranged and configured to extend over at least a portion of an upper belly and lower ribs of a user when the anterior trunk vest is worn by a user, the bottom section of the lower portion being adapted and configured, when a user is wearing the anterior trunk vest, to be secured around a user's right and left sides to the structure when the structure is positioned at least partly behind the user;
    shoulder straps connected to the top section of the lower portion such that, when the anterior trunk vest is worn by the user, each shoulder strap is attached to the top section at a location on an anterior of the user, each shoulder strap connected to the structure and comprising a second material and having a free end that is secured to the structure and each shoulder strap being configured to extend, when a user is wearing the anterior trunk vest and the shoulder straps are secured to the structure, from the top section of the lower portion over the shoulders of a user to the structure, the second material being more stretchable in a vertical direction than the first material is stretchable in a vertical direction such that, when the anterior trunk vest is positioned on a user and the bottom section of the lower portion and the shoulder straps are attached to the structure that is positioned at least partly behind the user, the user can lean forward away from the structure without the lower portion substantially crawling upward on the trunk of the user.

12. The combination of claim 11, wherein the first material comprises a leno weave fabric.

13. The combination of claim 11, wherein the first material is substantially more stretchable in a width direction than in a vertical direction.

14. The combination of claim 11, wherein the second material comprises foamed rubber.

15. The combination of claim 11, wherein the bottom section of the lower portion comprises swivel buckles for connecting the anterior trunk vest to the structure.

16. The combination of claim 11, wherein the anterior trunk vest is configured to be used as a harness.

17. The combination of claim 11, wherein the anterior trunk vest is configured to be used as a support.

18. The combination of claim 11, wherein the anterior trunk vest comprises a convergence zone for each side of the anterior trunk vest, the convergence zone located between the first material and the second material, the convergence zone for each side of the anterior trunk vest extending downward as the convergence zone extends outward when the anterior trunk support is worn by a user whose upper torso is upright.

19. A wheelchair comprising the combination of claim 11, wherein the structure comprises the wheelchair.

20. A backpack comprising the combination of claim 11, wherein the structure comprises the backpack.

* * * * *